United States Patent [19]

Muranushi

[11] Patent Number: 4,624,007

[45] Date of Patent: Nov. 18, 1986

[54] METHOD OF OBTAINING X-RAY CT IMAGE AND APPARATUS FOR UTILIZING THE SAME METHOD

[75] Inventor: Jun Muranushi, Ootawara, Japan

[73] Assignee: Tokyo Shibaura Denki Kabushiki Kaisha, Kawasaki, Japan

[21] Appl. No.: 582,603

[22] Filed: Feb. 22, 1984

[30] Foreign Application Priority Data

Feb. 24, 1983 [JP] Japan .................................. 58-30601

[51] Int. Cl.$^4$ .............................................. H05G 1/64
[52] U.S. Cl. ........................................ 378/4; 378/20; 378/99
[58] Field of Search ................. 378/4, 10, 20, 99, 901

[56] References Cited

U.S. PATENT DOCUMENTS

| | | | |
|---|---|---|---|
| 3,999,073 | 12/1976 | Hounsfield et al. | 250/445 |
| 4,044,260 | 8/1977 | Hounsfield | 250/360 |
| 4,105,922 | 8/1978 | Lambert et al. | 250/495 |
| 4,132,895 | 1/1979 | Froggatt | 250/445 |
| 4,245,244 | 1/1981 | Lijewski | 378/901 |
| 4,257,102 | 3/1981 | Horriba | 378/901 |
| 4,259,725 | 3/1981 | Andrews | 378/901 |
| 4,282,550 | 8/1981 | Coviello | 358/160 |
| 4,477,922 | 10/1984 | Liebetruth | 378/20 |

Primary Examiner—Craig E. Church
Assistant Examiner—Charles Wieland
Attorney, Agent, or Firm—Finnegan, Henderson, Farabow, Garrett & Dunner

[57] ABSTRACT

An X-ray CT diagnostic apparatus includes an unit for producing a scannogram of an object under examination, a unit for designating a plurality of slice positions on the scannogram by utilizing a line/marker generator, a unit for designating an interest region of the designated slice position in the scannogram, which is to be enlarged, by defining a center of the interest region by means of the line/marker generator, and a unit for enlarging and reconstructing the interest region of the designated slice position in such a manner that a center of the enlarged and reconstructed interest region is concident with the center of the interest region which has been designated in the scannogram.

4 Claims, 13 Drawing Figures

METHOD OF OBTAINING X-RAY CT IMAGE AND APPARATUS FOR UTILIZING THE SAME METHOD

BACKGROUND OF THE INVENTION

This invention relates to a method of obtaining an X-ray computerized-tomographic image and an apparatus for utilizing the above method, in which desirable regions of interest within tomographic images of an object are automatically enlarged and displayed at a correct position on the monitor screen.

The conventional X-ray computerized-tomographic apparatus set forth in the preamble has a function of displaying a scannogram and a tomographic image. That is, before data acquisition of the tomographic images of a diseased portion of the object under examination, the scannogram, which covers a wide region including that portion, is produced based upon the X-ray transmission detection signal. By observing the scannogram, positions for imaginary slices of the object, i.e., slice positions, for which the tomographic images are to be obtained are determined, and the tomographic images are obtained by reconstructing the other detection signal based upon the determined slice positions.

Further, when reconstructed tomographic images of the slice positions are observed, there may arise a necessity of enlarging part of an images (which are referred to as "interest regions") for the purpose of diagnosis. In this case, enlarged image are obtained from the other projection data (detection signal), which has been acquired in advance, by determining a center of the interest region for each tomographic image.

As previously described, in the conventional computerized-tomographic apparatus, when it is desirable to observe an enlarged tomographic image for the purpose of diagnosis, a center of the enlarged image of the interest regions must be determined for each of the tomographic images, which is a cumbersome task. Further, the operation of obtaining the enlarged images of the interest regions is also cumbersome. More particularly, first a scannogram is obtained, then slice positions are determined by observing the scannogram, and thereafter tomographic images are reconstructed. Subsequently the centers of the tomographic images of the interest regions which are to be enlarged are determined to obtain the enlarged image by observing the reconstructed tomographic images. Therefore, a long operation time is required until the enlarged image of the interest region is obtained from the projection data. Moreover, the patient must endure this long examination time.

An object of the invention is to provide an X-ray CT diagnostic apparatus which may overcome the conventional drawbacks described above and may permit a display of the enlarged tomographic images of the interest regions within the slice positions of the object in such that the centers of the enlarged interest region are always at the center of the display screen.

SUMMARY OF THE INVENTION

The above and other objects may be accomplished by providing an X-ray computerized-tomographic image apparatus comprising couch means for supporting the object under examination, couch drive means for controlling an interrupted transportation of the couch means along a longitudinal axis of the object, a source for irradiating fan-shaped X-rays, means for controlling projection of the fan-shaped X-rays toward the imaginary slice of the object through the X-ray source, means for detecting the fan-shaped X-rays which have penetrated through the slice of the object so as to produce selectively first and second detection signals, means for mounting the X-ray source and the detection means in such a manner that the X-ray source is positioned opposite from the detection means with respect to the slice of the object and for performing at least a relative revolution movement between the X-ray source and the detection means in a plane perpendicular to the longitudinal axis of the object and parallel to the slice of the object, system control means for performing control of the couch drive means, the mounting means, and the projection control means in such a manner that a first scanning mode for a scannogram of the object is effected by the interrupted transportation of the couch means while the X-ray source and the detection means remain at a given fixed position, and a second scanning mode for tomographic images of the imaginary slices of the object is effected by the relative revolution movement between the X-ray source the detection means and the object in each imaginary slice, operation control means for designating the imaginary slice of the object in the scannogram and a center of an interest region in the imaginary slice which is to be enlarged, memory means for storing a first data signal which is derived from the first detection signal for the scannogram of the object, and a second data signal which is derived from the second detection signal for the tomographic image of the object, data processing means for processing the first data signal which is read out from the memory means so as to produce the scannogram of the object in case of the first scanning mode and for processing the second data signal which is read out from the memory means so as to reconstruct and enlarge the interest region of the imarginary slice of the object which has been designated by the operation control means, whereby a center of the enlarged tomographic image of the interest region is coincident with the center of the interest region in the imaginary slice of the object, and monitor means for displaying at least the scannogram of the object and the enlarged tomographic image of the interest region selectively.

These objects may be also accomplished by providing a method of obtaining an X-ray tomographic image of an object, comprising the steps of directing interruptedly fan-shaped X-rays from an X-ray source through the object so as to produce selectively first and second X-ray images, detecting selectively first and second detection signals from the first and second X-ray images by an X-ray detector, performing first and second scanning modes by controlling operations of a relative movement among the X-ray source, the X-ray detector and the object, storing first and second data signals in a memory device, which are derived from the first and second detection signals during the first and second scanning modes respectively, processing the first data signals, which are read out from the memory device so as to produce a scannogram of the object, designating in the scannogram imaginary slices of the object, centers of interest regions of the imaginary slices which are to be enlarged, and an enlarging size of the interest regions, and reconstructing the second data signals obtained during the second scanning mode so as to enlarge tomographic images of the designated interest region of the imaginary slice in the scannogram, whereby a center of the enlarged tomographic image of the designated interest region is coincident with the center of the designated interest region.

According to the invention, the imaginary slice position to be scanned can be designated by displaying a line on a displayed scannogram, and the center of the interest region within the displayed scannogram can be designated by displaying a marker superimposed on the line on the scannogram, and further the degree by which the interest regions are enlarged can be determined by observing the scannogram. Thus, an enlarging and reconstruction operation can be done with respect to the desirable interest regions. The enlarged and reconstructed tomographic images of the desirable interest region can be displayed with their centers at the center of the display screen, so that it is possible to permit accurate tomographic image diagnosis.

Further, the target tracking can be done directly on the scannogram, so that the time required for enlarging the CT images can be greatly reduced, thereby shortening the entire diagnostic time period.

BRIEF DESCRIPTION OF THE DRAWINGS

The above and other objects and features of the present invention may be best understood by reference to the specification and the accompanying drawings, in which.

DETAILED DESCRIPTION OF THE PREFERRED EMBODIMENTS

Figure 1:
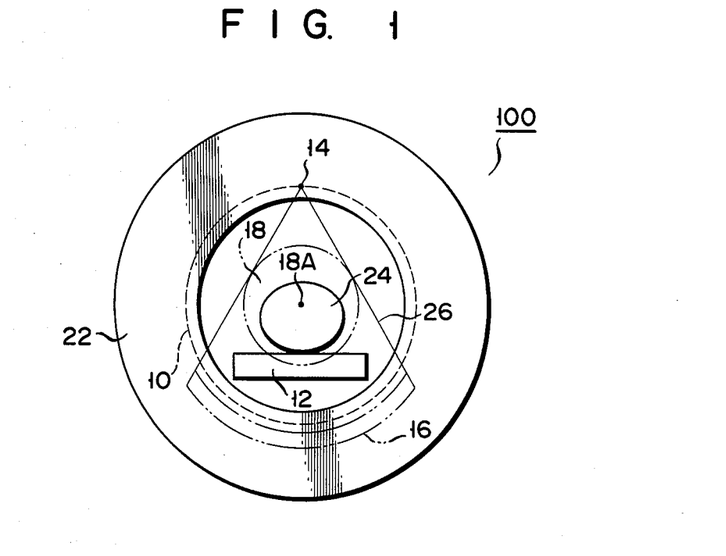
FIG. 1 is an illustration of an X-ray projection in a gantry.

FIG. 1 illustrates relative positions of main components which constitute an X-ray computerized-tomographic apparatus (referred to as an "X-ray CT apparatus") according to one preferred embodiment.

Referring to the drawing, the X-ray CT apparatus 100 comprises a gantry 22, which includes an X-ray tube 14 and an X-ray detector 16, having a plurality of detector elements. The X-ray tube 14 and X-ray detector 16 face each other and can be rotated along a circle with the center thereof at a center 18A of a data acquisition regions 18. The X-ray tube 14 can project. fan-shaped X-ray beams 26 onto an object 24 under investigation, e.g., a patient, disposed on a couch 12 in the data acquisition region 18. The apparatus 100 can reconstruct a tomographic image of the object 14 at an interest region within the slice position by a tomographic image reconstruction device (which will be described later), and display the tomographic image on a picture monitor, also described later.

A detailed description of the gantry 22 and the relevant components will now be given with reference to FIG. 2.

Figure 2:
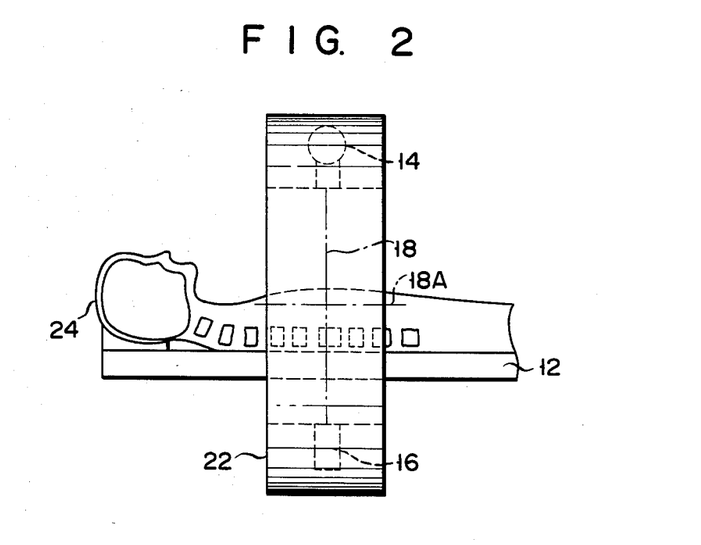
FIG. 2 is a side view of an object and the gantry shown in FIG. 1.

As shown in FIG. 2, the X-ray tube 14 and X-ray detector 16 of the gantry 22 face each other and are rotated along a circle with the center thereof at the center 18A of the data acquisition region 18, while the fan-shaped X-ray beams 26 are interruptedly projected from the X-ray tube 14 onto the object 24 under investigation, which is disposed on couch 12 in the data acquisition region 18. The gantry 22 as a whole can be tilted with respect to the longitudinal axis of the object 24, and also can be rotated in a plane perpendicular to the longitudinal axis.

Figure 3:
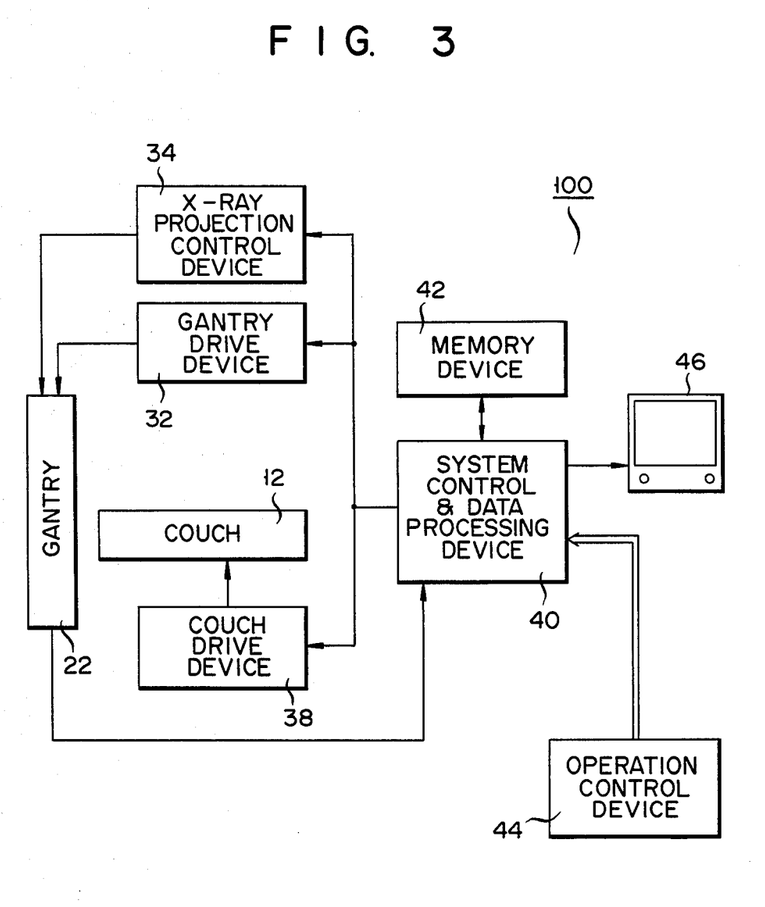
FIG. 3 is a block diagram of an X-ray CT apparatus, except an X-ray radiation construction, according to one preferred embodiment.

FIG. 3 shows an entire system of the X-ray CT apparatus 100. A gantry drive device 32 controls the relative revolution movement between the X-ray tube 14 and the detector 16 provided in the gantry 22. An X-ray projection-control device 34 can receive a control signal from a system control & data processing device 40 and applies a predetermined voltage and current to the X-ray tube 14 at a predetermined time. The X-ray tube 14 is thus controlled to project the X-ray beams 26 toward the object 24.

The couch 12 is slidable by a couch drive device 38 within the data acquisition region 18 of the gantry 22 in a direction parallel to the longitudinal axis of the object 24.

Figure 4:
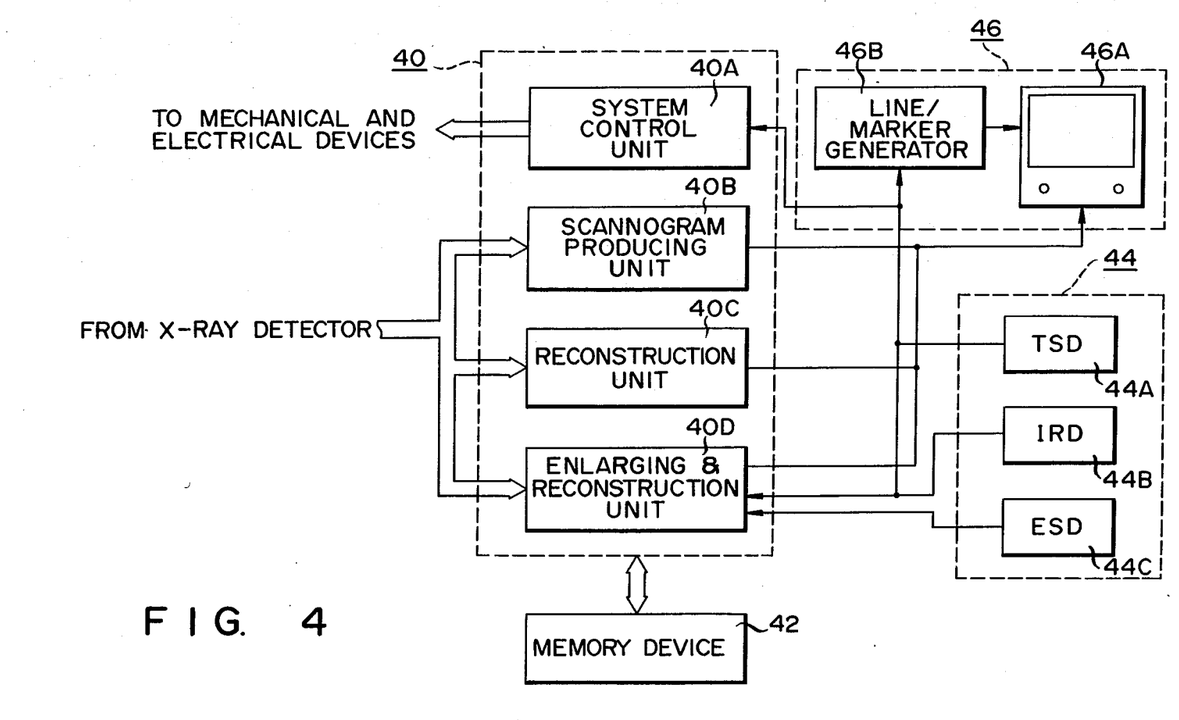
FIG. 4 is a block diagram of the main circuit construction of the apparatus shown in FIG. 3.

The system control & data processing device 40 (which is hereinafter referred to merely as "processing device"), as shown in FIG. 4, is composed of a system control unit 40A, a scannogram producing unit 40B, a reconstruction unit 40C, and an enlarging and reconstruction unit 40D.

The system control unit 40A controls the entire system of the X-ray CT apparatus 100 according to a control signal from an operation control device 44. It can also provide the control signal to the gantry drive device 32 and the couch drive device 38 to permit X-ray projection with respect to the imaginary slices, designated by a tomographic slice designation unit 44A in the control operation device 44. The scannogram producing unit 40B can produce a transmission image (a scannogram) of the object 24 based upon X-ray transmission data produced from the detector 16 by analogue-to-digital conversion of the detection signal (a first detection signal) when the X-ray projection is executed in such a manner that the X-ray tube 14 and the detector 16 are held at a fixed angular position with respect to the object 24 while interruptedly moving the object 24 disposed on the couch 12 in a direction parallel to the longitudinal axis of the object 24. The reconstruction circuit 40C reconstructs tomogaphic images of the designated imaginary slice according to projection data obtained from the detector 16 as a second detection signal, which detects the X-ray beams which are projected from the X-ray tube 14 while tube 14 is revolving about the object 24 and transmitted therethrough. The enlarging & reconstruction unit 40D can reconstruct and enlarge a particular area (i.e. an interest region) of an imaginary slice according to the projection data as the second detection signal, which has been designated by an interest-region designation unit 44B and an enlarged size designating unit 44C in the control operation device 44.

A memory device 42 can store a first data signal which is derived from the first detection signal for the scannogram of the object and a second data signal which is derived from the second detection signal for the tomographic image, and also first and second image data signals for the scannogram and the tomographic images obtained by the scannogram producing unit 40B, the reconstruction unit 40C and the enlarging and reconstruction unit 40D.

The operation control device 44 has a keyboard for inputting an operation start command and X-ray projection conditions, and it includes the tomographic slice designating unit 44A, the interest region designating unit 44B, and the enlarged size designating unit 44C. The projection conditions involve the slice positions, the position of the interest region and the enlarged size of the interest region. The tomographic slice designating unit 44A serves to superimpose the lines $S_1 \sim S_n$ on a scannogram displayed on the screen of the picture monitor 46A of the image display device 46. Those lines are generated by a line/marker generator 46B under the control of this unit 44A. Also, the designating unit 44A provides co-ordinate data for designating a tomographic slice. This data is necessary for driving the couch drive device 38, gantry drive device 32 and X-ray protection control device 34 through the system control unit 40A. The interest-region designating unit 44B provides co-ordinate data for setting the center of the interest region by displaying a marker $P_1 \sim P_n$ on the given line displayed on the screen (the scannogram) of the picture monitor 46A. The marker is also generated by the line/marker generator 48 under the control of this unit 44B. The enlarged size designating unit 44C determines the enlarged size of the interest region in the designated tomographic slice. The tomographic-slice designating unit 44A and interestregion designating unit 44B may be constructed with a track ball, for instance. The image display unit 46 includes the picture monitor 46A and the above-described line/marker generator 46B. The picture monitor 46A displays scannograms and tomographic images selectively. The line/marker generator 46B produces brightness signals for displaying the lines $S_1 \sim S_n$ and markers $P_1 \sim P_n$ on the picture monitor 46A from the co-ordinate data received from the tomographic slice designating unit 44A and interest region designating unit 44B.

The operation of the X-ray CT apparatus 100 shown in FIG. 4 will now be described with reference to FIG. 5.

First, a scannogram is produced and displayed as shown in a step 1 in the left column (operation flow) of the flow chart of FIGS. 5A through 5D. More specifically, referring to FIGS. 1 to 4, the fan-shaped X-ray beams 26 are projected from the X-ray tube 14 mounted in the gantry 22 onto the object 24, i.e., patient lying on the couch 12, by intermittently moving the object 24 in the data acquisition region 18 in the horizontal direction (i.e., the longitudinal axis of the object 24) in FIG. 2, while the X-ray tube 14 and the detector 16 are held fixed at a predetermined position with respect to the object 24. A transmitted X-ray detection signal from the detector 16 is first supplied to the memory device 42 as a first (projection) data signal, and then supplied to the scannogram producing unit 40B in the system control & data processing device 40. The scannogram producing unit 40B produces a scannogram from the first data signal. This first data signal is again supplied to the memory device 42 to be stored in a file 2 therein (see FIG. 5A). At the same time, the unit 40B supplies it to the image display device 46 to display the scannogram of the object 24 on the picture monitor 46A, as shown in the center column (hardware) of FIGS. 5A and 5B.

Figure 5A:
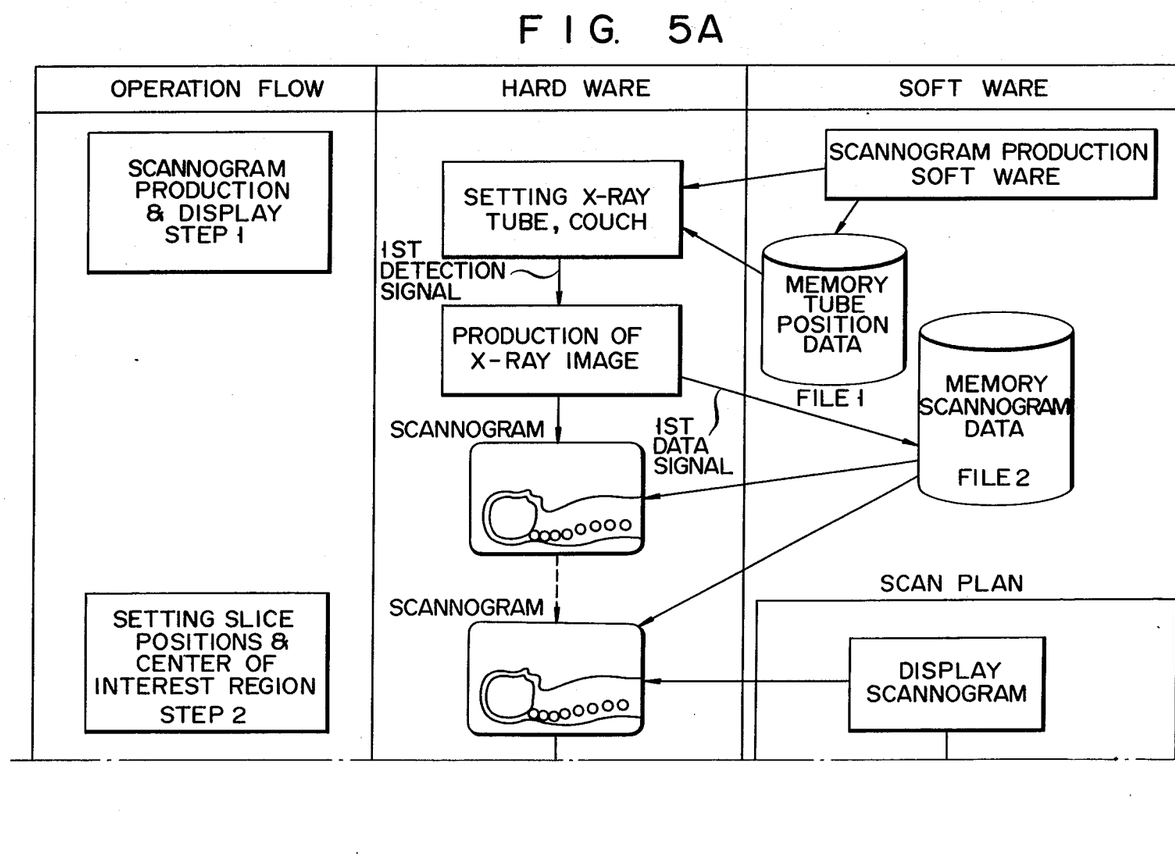
FIGS. 5A to 5D illustrate the entire operation of the enlarging and reconstructing as executed in the apparatus shown in FIG. 3.
Figure 5B:
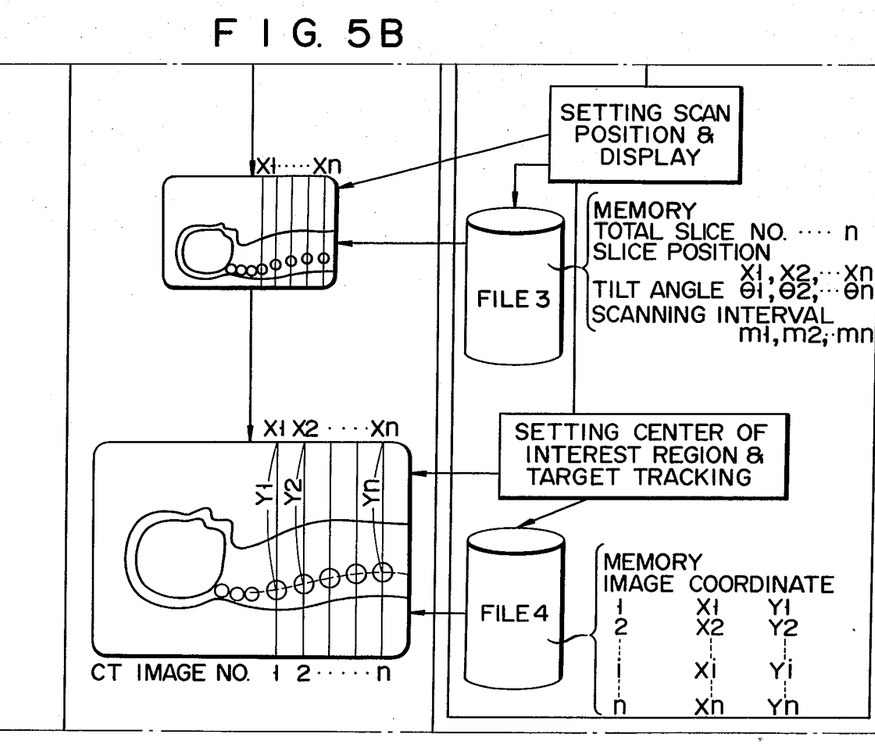

More specifically, setting the position of the X-ray tube 14 and setting the couch 12 relative to the X-ray tube 14 are executed according to scannogram production software, as shown in the right column of FIG. 5A, and hardware, as shown in the center column thereof. More particularly, the X-ray projection control device 34 and couch drive device 38 are controlled by reading out the position data stored in the file 1 of the memory device 42 according to the software (see FIG. 5A). Then, the scannogram data signal (first detection signal) is obtained from the X-ray detector 16 by projecting the fan-shaped X-ray beams 26 from the X-ray tube 14 onto the object 24 several times (e.g., 320 times) while holding the X-ray tube 14 and the detector 16 at a fixed position and transporting the object 24 in the direction parallel to the longitudinal axis of the object 24. That is, the first detection signal is A/D converted into a corresponding detection signal in a digital form, which is then processed into the scannogram data signal. The resultant data signal is stored in the file 2 of the memory device 42. Then, based upon the scannogram data stored in the file 2, the scannogram of the object 24 is displayed on the picture monitor 46A according to the scannogram display software, as shown in the center column of FIG. 5B.

Subsequently, slice positions for tomographic images and the center of region of interest are set in a step 2.

Figure 6:
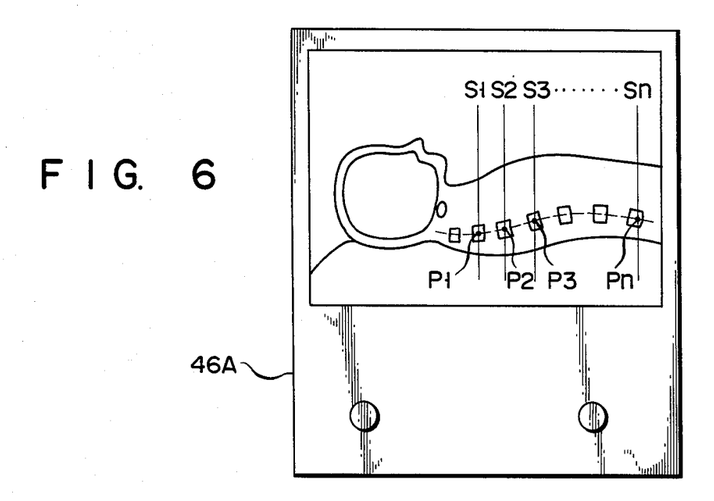
FIG. 6 shows a scannogram displayed on a picture monitor.

More specifically, the operator manipulates the operation control device 44 while watching the scannogram to supply co-ordinate data $X_i$, $Y_i$ ($i=1\sim n$) from the tomographic slice designating unit 44A to the line/marker generator 46B. Thus, line $S_1, S_2, \ldots, S_n$ designating the slice positions for tomographic images, as shown in an enlarged scale in FIG. 6, are displayed on the picture monitor 46A according to the brightness signals provided from the line/marker generator 46B. The co-ordinate data $X_i$, $Y_i$ is also supplied to the system control unit 40A. The system control unit 40A calculates data necessary for the X-ray projection on the designated slice positions, such as the scanning intervals $m_1, m_2, \ldots, M_n$, the driving timing of the couch 12, and the drive timing and tilt angles $\theta_1, \theta_2, \ldots, \theta_n$ of the gantry 22, according to the input co-ordinate data. The operator also uses the operation control device 44 while watching the scannogram to supply co-ordinate data from the interest region designating unit 44B to the line/marker generator 46B. Thus, the markers $P_1, P_2, \ldots, P_n$ for designating the centers of the interest regions are superimposed on the lines $S_1, S_2, \ldots, S_n$ which have been displayed on the picture monitor 46A according to a brightness signal provided from the line/marker generator 46B as shown in FIG. 6.

More specifically, in the step 2, the scan positions (corresponding to co-ordinate data $X_i$) are determined by the line/marker generator 46B while the lines $S_1, S_2, \ldots, S_n$ are displayed on the scannogram. Also, the number of CT images necessary for data acquisition, their scanning positions, and scanning intervals $m_1, m_2, \ldots, m_n$ are stored in the file 3 of the memory device 42. Then the centers of interest regions are determined on the scannogram on the picture monitor 46A while the markers are displayed as $P_1, P_2, \ldots, P_n$ on the scannogram by means of the line/marker generator 46B. In this embodiment, a series of the operation of determining the slice positions $S_1, S_2, \ldots, S_n$ and then determining the centers of the interest regions $P_1, P_2, \ldots, P_n$ is referred to as "target tracking". The sequence of operations of such target tracking is referred to as a scan plan (the right column of FIGS. 5A and 5B).

It is one of the features according to the invention that the target tracking can be executed directly on the scannogram.

Subsequently, the step 3 of deciding to enlarge the size of the designated interest region is executed.

Figure 5C:
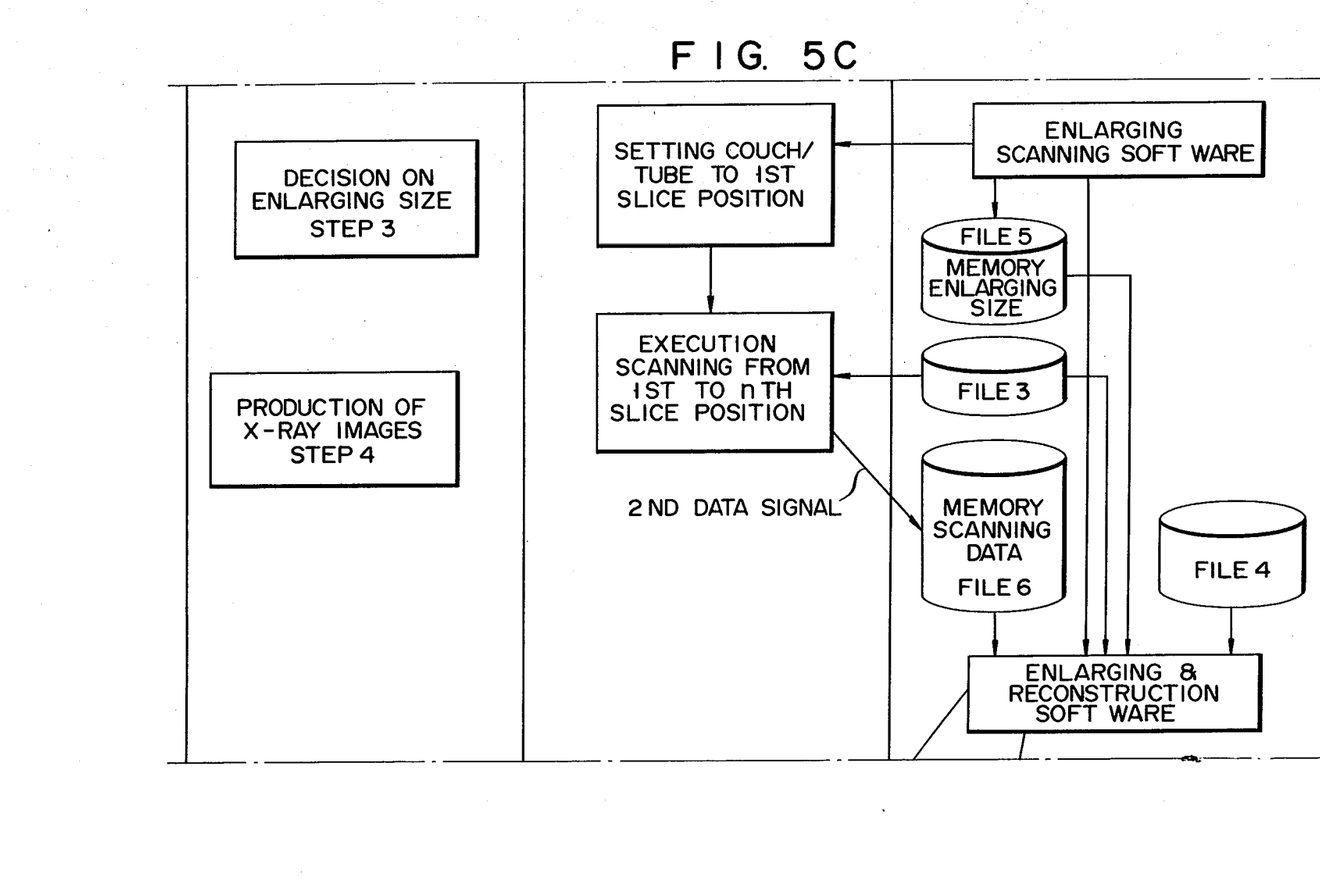

More specifically, in the step 3, the operator manipulates the control operation device 44 to supply data to enlarge the size of the interest region of the tomographic slice, which is stored in a file 5 of the memory device 42, from the enlarged-size designating unit 44C to the enlarging and reconstructing unit 40D. By the above operation, the tomographic position, center of interest region and enlarged size are determined as shown in FIG. 5C. The couch 12 is interruptedly moved by the couch drive device 38 in a direction parallel to the longitudinal axis of the object 24 by a control signal, provided from the system control unit 40A in the system control & data processing device 40 according to the scanning hardware in the right column in FIG. 5C. The couch movement is carried out in such that a plane involving a tomographic slice of the object 24, designated by the line $S_1$ (corresponding to the first slice position) is coincident with the plane of rotation of the X-ray tube 14. Then the gantry 22 is rotated around the object 24 by the gantry drive device 32, and the X-ray protection control device 34 causes the X-ray tube 14 to project the X-ray beams 26 intermittently onto the object 24 while rotating the gantry 22. This X-ray projection is done for the purpose of the known CT image acquisition. The projection data or scanning data derived from the detector 16 every time the X-ray projection is converted by the A/D converter, to be described later, into a digital value, which is transferred to the enlarging & reconstruction unit 40D. When the X-ray projection on that first tomographic slice position of the object 24 specified by the line $S_1$ is completed, the couch 12 is moved by a given distance, and the succeeding X-ray projection is done on a second tomographic slice position of the object 24, specified by the line $S_2$. Then, further X-ray projection is done on a third tomographic slice position specified by the line $S_3$. This sequential projection operation is carried out up to the last slice position specified by the line $S_n$. All projection data obtained for the individual slice positions ($S_1, S_2, \ldots, S_n$) are dealt with in the enlarging and reconstruction unit 40D for enlarging and reconstruction, which will be described later in detail. The image data that is obtained in the above enlarging and reconstruction unit 40D is stored in a file 7 of the memory device 42.

Figure 5D:
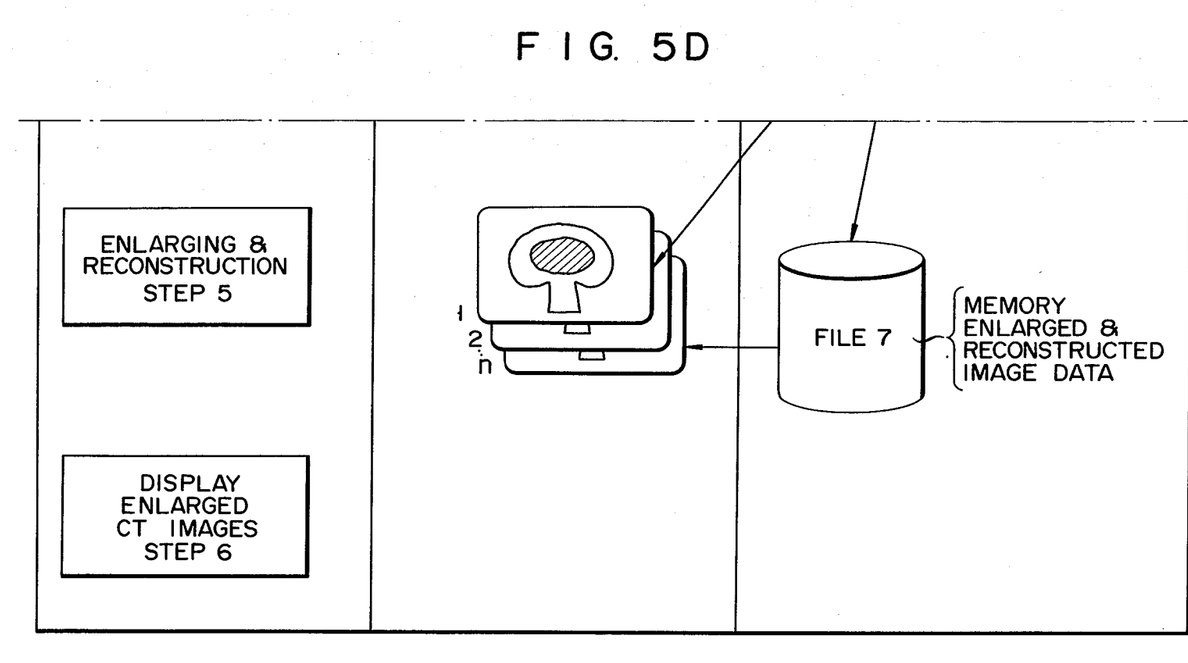

Thereafter, a last step 6 is executed (see FIG. 5D). In this step, the enlarged and reconstructed image data is read out from the file 7 and supplied to the picture monitor 46A. In this way, the enlarged CT images of the first to the last interest regions designated by the lines $S_1$ to $S_n$ are successively displayed on the picture monitor 46A.

Now, the enlarging and reconstruction operation of the step 5 just desired will be described in more detail.

Figure 7:
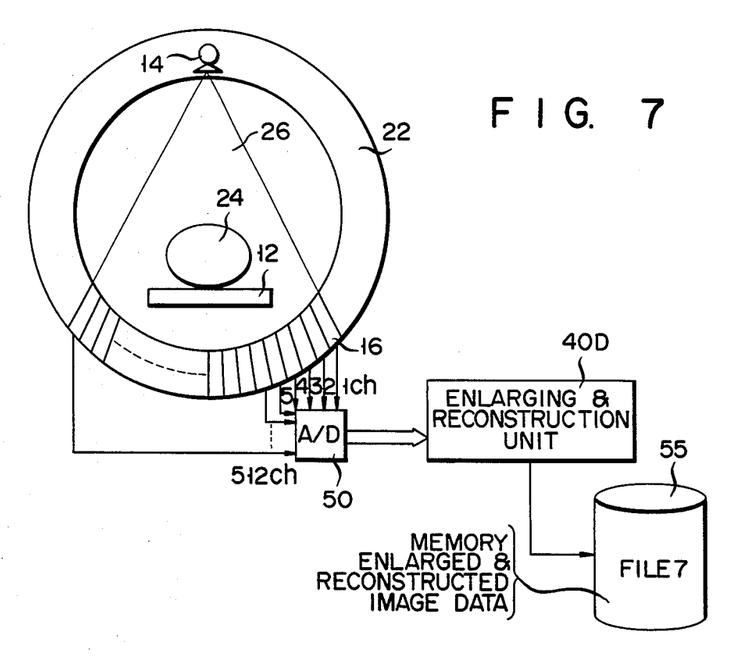
FIG. 7 is a schematic diagram of the enlarging and reconstructing image operation.

FIG. 7 shows a basic construction of the enlarging & reconstruction operation which is substantially the same as that shown in FIG. 1, and like components are not furthermore described.

The fan-shaped X-ray beams 26, projected from the X-ray tube 14, is transmitted through the object 24 to be incident on the X-ray detector 16. In this embodiment, the detector 16 has 512 channels, and therefore 512 detection signals (=the first detection signal) are supplied from 512 channels of the detector 16 to an A/D converter 50.

In other words, in the acquisition of projection data for producing X-ray CT images as well as the scannogram, 512 pieces of projection data signals (i.e., the first or second detection signal) are obtained in one projection.

As is known, in the production of the scannogram (step 1), the X-ray tube 14 and detector 16 are set at fixed positions relative to the object 24, and X-ray projection is done, for example, 250 times, at a predetermined transfer pitch of the couch 12 in a direction parallel to the longitudinal axis of the object 24. That is, 250 pieces of projection data signal (i.e., the first data signal) are acquired fo obtaining one scannogram.

Figure 8:
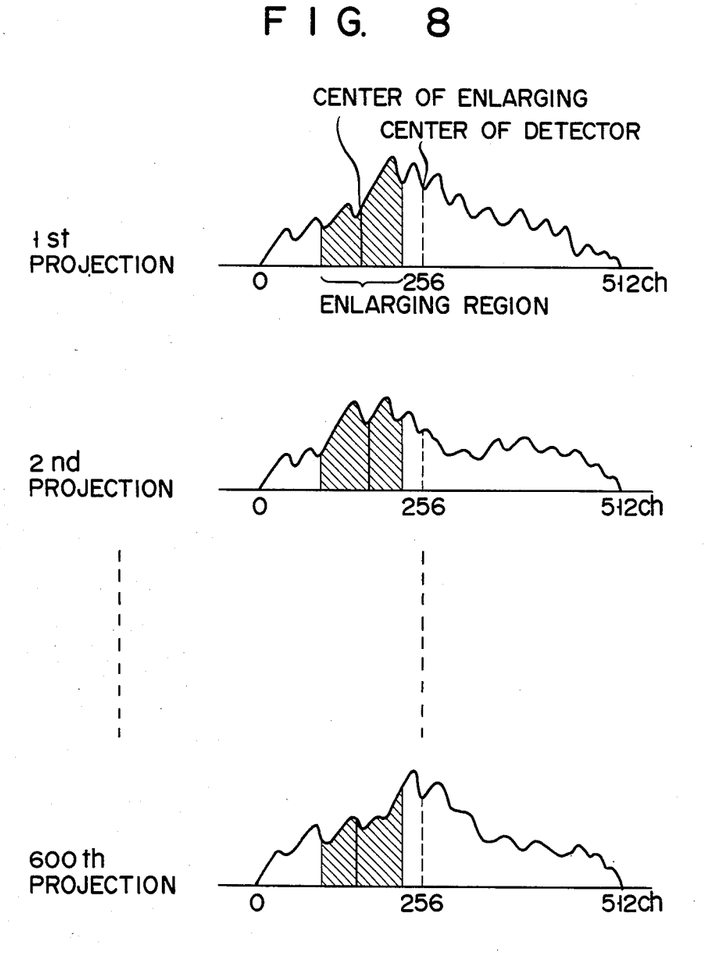
FIG. 8 is an illustration of the projection data with reference to the enlarging operation in FIG. 7.

In contrast with this, in the CT image data acquisition, the projection data signal (i.e., the second data signal) is obtained by rotating the X-ray tube 14 and detector 16 by 360° about the object 24. In this embodiment, the tilt angle of the gantry 22 is set to 0°, the revolution pitch angle is to 0.6°, and the X-ray beams 26 is projected 600 (,i.e., $360° \div 0.6° = 600$) times onto the first slice position $S_1$. In other words, in this embodiment, to obtain one CT image for one slice position, (307,200) detection signals (i.e., the second detection signal) are obtained from the 512-channel detector 16 by effecting the X-ray projection 600 times ($512 \times 600 = 307,200$). One set of projection data signal is constituted by 512 detection signals as schematically shown in FIG. 8.

The A/D converted projection signal (i.e., the second detection signal) in a digital form is subsequently dealt with in the enlarging and reconstruction unit 40D as previously described in conjunction with the step 5. The enlarged and reconstructed image data is stored in the file 7 of the memory device 42. Thereafter, enlarged CT images are displayed in turn on the picture monitor 46A as described in connection with the step 6.

The enlarging will now be described in more detail. In the step 2, a center of enlarging is determined for each interest region of the slice positions $S_1, S_2, \ldots, S_n$ while observing the scannogram, that is, the above-described target tracking is executed, and the data thus obtained in stored in the file 4 of the memory device 42. The center of enlarging position varies for each projection with representing a sine wave (see FIG. 8).

As previously described in detail, according to the invention the center of the enlarged interest region can be determined by executing the target tracking directly in the scannogram, not the CT images.

The projection data obtained in the step 4 is enlarged and reconstructed in the step 5 based upon the target tracking data stored in the file 4 and enlarged size data obtained in the step 3.

Figure 9:
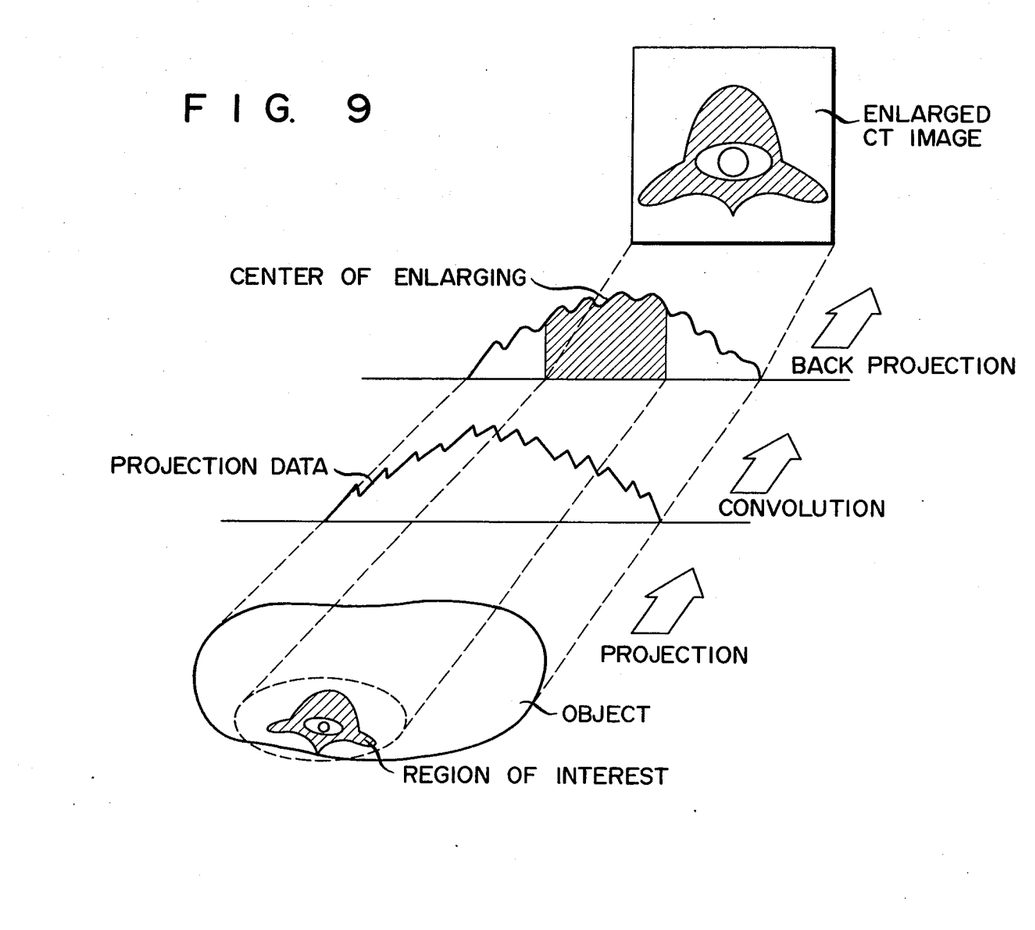
FIG. 9 is an illustration on the enlarged CT image with reference to the enlarging operation in FIG. 7.

FIG. 9 schematically illustrates the enlarging system of the interest region of the object according to the invention.

While the invention has been described in terms of certain preferred embodiments and examplified with respect thereto, those skilled in the art will readily appreciate that various modifications, changes, omissions and substitutions may be made without departing from the spirit of the invention.

For example, in the above embodiment, setting of the interest region with respect to the backbone has been done using solely the side scannogram of the object. Where the backbone position changes three-dimensionally, the centers of the enlarging in the interest regions $P_1, P_1', P_2, P_2', \ldots$ can be determined more accurately in the following way.

Figure 10:
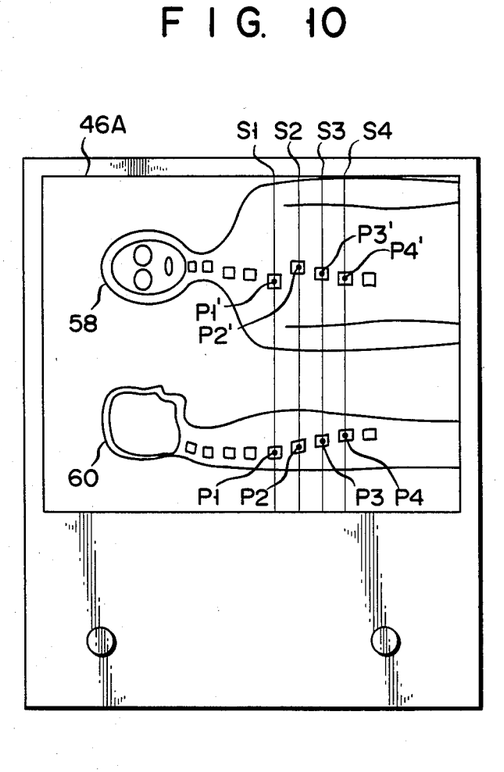
FIG. 10 is another scannogram displayed on the TV monitor according to another preferred embodiment.

As shown in FIG. 10, a top scannogram 58, of the object 24 obtained by the first X-ray projection from the X-ray tube 14 which is set right above the object 24, and a side scannogram 60 thereof, obtained by the second X-ray projection from the X-ray tube 14 set on one side of the object 24, are simultaneously displayed on the picture monitor 46A. The center of the interest region is specified by displaying two markers P and P' on each of the lines $S_1, S_2, \ldots$ which are common to both top and side scannograms 58 and 60. With the centers of the interest region designated by displaying two markers, the enlarged and reconstructed image for the interest region can be displayed more accurately.

What is claimed is:

1. A method for obtaining enlarged X-ray computerized tomographic images in cross-sectional planes of an object under examination at a plurality of designated positions along a curved line, comprising the steps of:
   projecting a fan-shaped radiation beam toward the object;
   receiving that portion of said fan-shaped radiation beam that has penetrated through the object so as to produce projection data representative of that penetration;
   translating the object along the longitudinal axis of the object to obtain a scannogram of the object from said projection data;
   displaying said scannogram;
   displaying, superimposed upon said scannogram, a plurality of line markers;
   manually aligning said line markers with a plurality of corresponding designated positions of said object along said curved line at which the enlarged tomographic images are to be taken;
   displaying, superimposed upon said line markers, a plurality of center marks;
   manually aligning said center markers with the centers of said designated positions;
   successively positioning said source means relative said object in response to said manual alignment of said line markers, to align said fan-shaped beam along said object at successive ones of said designated positions;
   effecting a rotation of said source means about the object at each of said successive designated positions to acquire projection data viewed from different directions at said successive designated positions;
   reconstructing, in response to both said projection data obtained from said second control means and to said manual alignment of said center markers, enlarged images of said object the centers of which correspond to the centers of said designated positions as evidenced by the locations of said center markers on said displayed scannogram; and
   displaying said enlarged tomographic images.

2. The method according to claim 1, wherein:
   said step of translating includes obtaining two different scannograms, one being a top view of said object and the other being a side view of said object;
   said step of displaying said scannogram includes displaying both of said scannograms;
   said step of manually aligning said line markers includes aligning said line markers through both of said displayed scannograms;
   and said step of manually aligning said center markers includes aligning said center markers on both of said displayed scannograms to further define the locations in said object of said centers of said designated locations.

3. An X-ray computerized tomographic apparatus for obtaining enlarged X-ray computerized tomographic images in cross-sectional planes of an object under examination at a plurality of designated positions along a curved line, comprising:
   source means for projecting a fan-shaped radiation beam toward the object;
   detector means for receiving that portion of said fan-shaped radiation beam that has penetrated through the object so as to produce projection data representative of that penetration;
   first control means for translating the object along the longitudinal axis of the object to obtain a scannogram of the object from said projection data;
   display means for displaying said scannogram, for displaying superimposed upon said scannogram a plurality of line markers which are manually alignable on said scannogram with a plurality of corresponding designated positions of said object along said curved line at which the enlarged tomographic images are to be taken, and for displaying superimposed upon said line markers a plurality of center markers which are manually alignable with the centers of said enlarged designated positions:
   addressing means, responsive to said manual alignment of said line markers, for successively positioning said source means relative said object to align said fan-shaped beam along said object at successive ones of said designated positions;
   second control means for effecting a rotation of said source means about the object at each of said successive designated positions to acquire projection data viewed from different directions at each of said successive designated positions;
   reconstructing means, responsive to both said projection data obtained from said second control means and to said manual alignment of said center markers, for reconstructing enlarged images of said object, the centers of said images corresponding to the centers of said designated positions as evidenced by the locations of said center markers on said displayed scannogram; and
   said display means further including means for displaying said enlarged tomographic images.

4. The apparatus according to claim 3, wherein said first control means obtains two different scannograms, one being a top view of said object and the other being a side view of said object; said display means includes means for displaying both of said scannograms; said means for manually aligning said line markers includes means for manually aligning said line markers through both of said displayed scannograms; and said means for manually aligning said center markers includes means for manually aligning said center markers on both of said displayed scannograms to further define the locations in said object of said centers of said designated positions.

* * * * *